United States Patent [19]

Ionescu et al.

[11] 4,388,735
[45] Jun. 21, 1983

[54] LOW PROFILE PROSTHETIC XENOGRAFT HEART VALVE

[75] Inventors: Marian I. Ionescu, Leeds, England; Jay A. Lenker, Laguna Beach, Calif.; Robert F. Rosenbluth, Laguna Niguel, Calif.; Louis Seiler, Jr., Huntington Beach, Calif.

[73] Assignee: Shiley Inc., Irvine, Calif.

[21] Appl. No.: 203,804

[22] Filed: Nov. 3, 1980

[51] Int. Cl.³ .............................................. A61F 1/22
[52] U.S. Cl. ........................................................ 3/1.5
[58] Field of Search ........................................ 3/1.5, 1

[56] References Cited

U.S. PATENT DOCUMENTS

| | | | |
|---|---|---|---|
| 3,197,788 | 8/1965 | Segger | 3/1.5 |
| 3,714,671 | 2/1973 | Edwards et al. | 3/1.5 |
| 4,084,268 | 4/1978 | Ionescu et al. | 3/1.5 |
| 4,120,649 | 10/1978 | Schechter | 3/1.5 X |
| 4,172,295 | 10/1979 | Batten | 3/1.5 |
| 4,291,420 | 9/1981 | Reul | 3/1.5 |
| 4,299,753 | 4/1981 | Liotta et al. | 3/1.5 |

FOREIGN PATENT DOCUMENTS 1264472 2/1972 United Kingdom ................... 3/1.5

OTHER PUBLICATIONS

"Frame-Mounted Tissue Heart Valves: Technique of Construction", by Ivan T. Bartek et al., Thorax (1974), 29, 51, pp. 51-55.

Primary Examiner—Ronald L. Frinks
Attorney, Agent, or Firm—Knobbe, Martens

[57] ABSTRACT

Prosthetic heart valves comprising an annular, right cylindrical, metal stent covered with fabric to which a glutaraldehyde-stabilized pericardial valving element formed of three leaflets, each having a plateau on a truncated triangle extending higher at the center than at the edges, and formed as a cylinder having a diameter substantially equal to the diameter of the stent, and having a low profile is disclosed.

34 Claims, 11 Drawing Figures

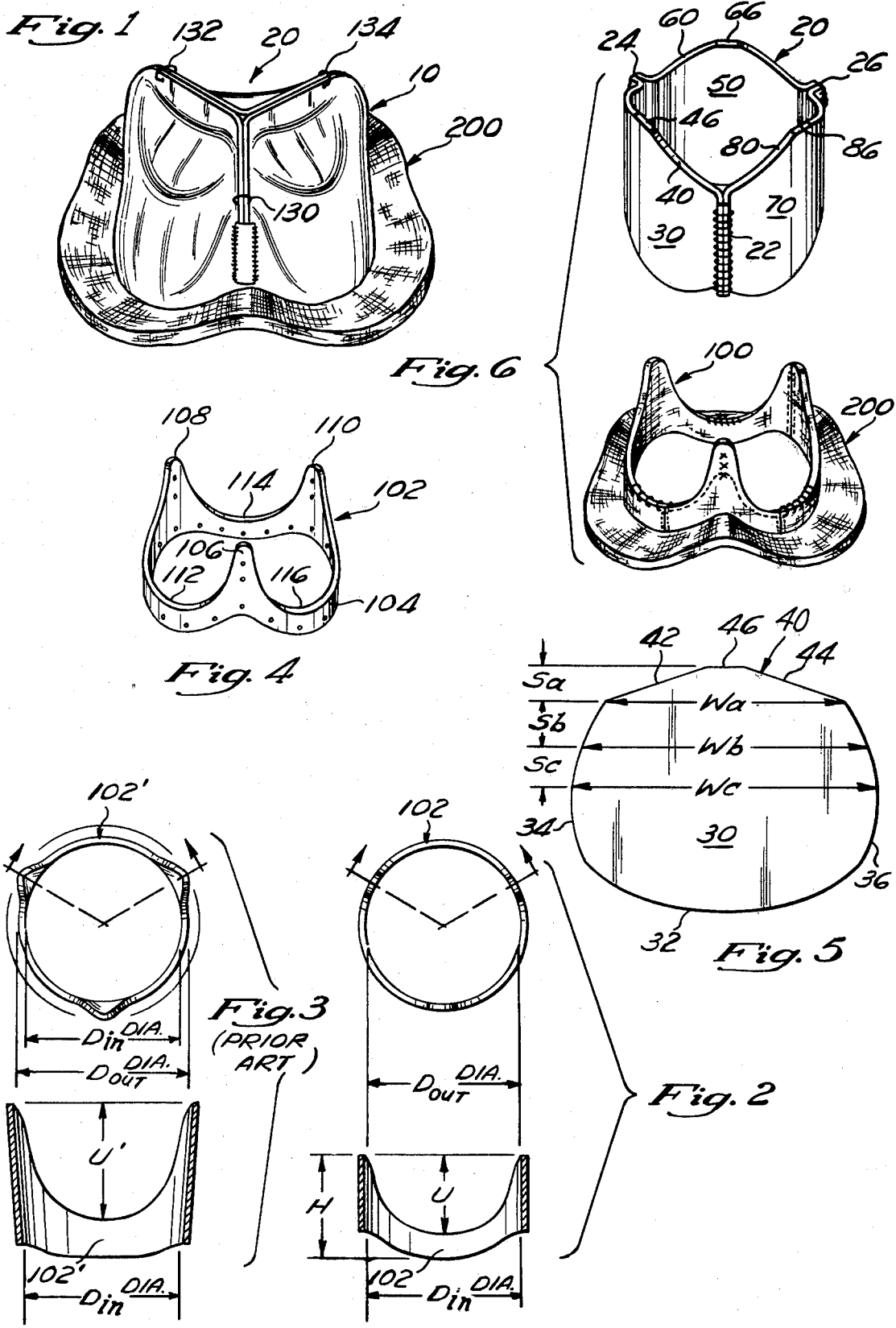

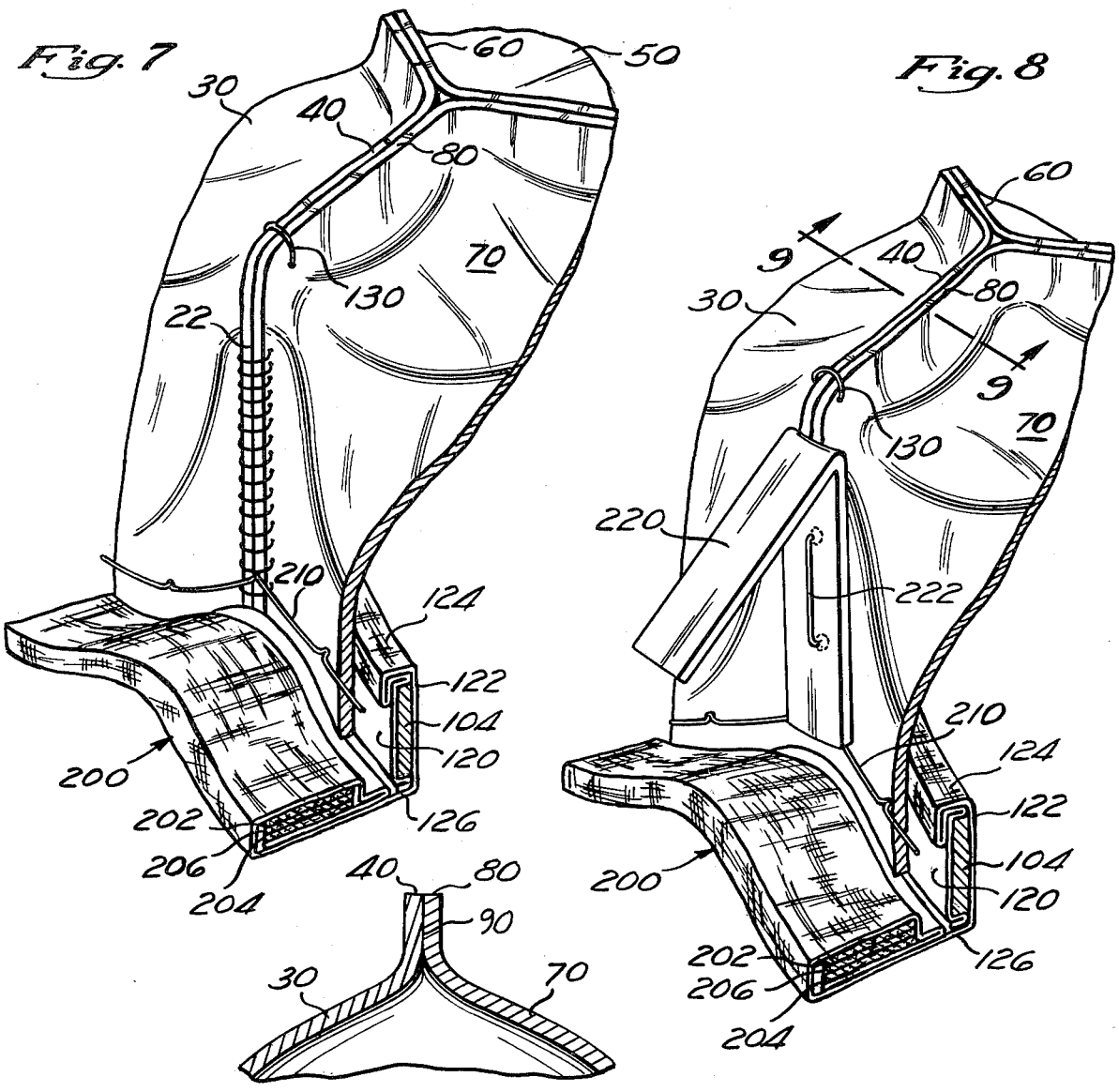

LOW PROFILE PROSTHETIC XENOGRAFT HEART VALVE

TECHNICAL FIELD

The early development of prosthetic heart valves is well documented in papers given at symposia in 1960 and in 1968, published in PROSTHETIC HEART VALVES, Lyman A. Brewer III, Ed., Charles C. Thomas Publishing Co., Springfield, Ill. (1969), Second National Conference on Prosthetic Heart Valves; PROSTHETIC VALVES FOR CARDIAC SURGERY, K. Alvin Merendino, Editor, Thomas Publishing Co., Springfield, Ill. (1961).

Lefrak and Starr recently surveyed the development of cardiac valve prostheses, E. A. Lefrak, and A. Starr, CARDIAC VALVE PROSTHESES, Appleton-Century-Krofts, New York, 1979 and the development of tissue heart valves has been comprehensively reviewed, Ionescu, Marian I., TISSUE HEART VALVES, Butterworths, Boston, 1979.

Great efforts have been expended in the development of tissue heart valve prostheses and in the development of supportive structures, or stents, for tissue valves. Representative of efforts to develop stents for tissue valves are the disclosures in the following U.S. Pat. Nos.: 3,570,014, W. D. Hancock, Mar. 16, 1971; 3,714,671, William Sterling Edwards, et al., Feb. 6, 1973; 3,755,823, W. D. Hancock, Sept. 4, 1973; 3,983,581, William W. Angell, Oct. 5, 1976; 4,035,849, William W. Angell et al., July 19, 1977; 4,079,468, Domingo Santo Liotta, Mar. 21, 1978; 4,084,268, Marian I. Ionescu et al., Apr. 18, 1978; 4,106,129, Alain F. Carpentier, et al., Aug. 15, 1978; 4,172,295, Richard J. Batten, Oct. 30, 1979 and 4,192,020, Richard B. Davis, et al., Mar. 11, 1980. Other structures are also reported in the aforementioned treatises on heart valve developments.

A number of specific tissue valves are described in the following publications:

W. Sterling Edwards, et al., MITRAL AND AORTIC VALVE REPLACEMENT WITH FASCIA LATA ON A FRAME, Journal of Thoracic & Cardiovascular Surgery, Volume 58, No. 6, December 1969, Pages 854–858; Ionescu, M. I., et al., HEART VALVE REPLACEMENT WITH IONESCU-SHILEY PERICARDIAL XENOGRAFT, Cardiology Digest, June, 1977, Page 45; Ionescu, M. I., et al., HEART VALVE REPLACEMENT WITH THE IONESCU-SHILEY PERICARDIAL XENOGRAFT, The Journal of Thoracic and Cardiovascular Surgery, Volume 73, Pages 31–42, 1977; Tandon, A. P., et al., LONG-TERM HAEMODYNAMIC EVALUATION OF AORTIC PERICARDIAL XENOGRAFT, British Heart Journal, Volume 40, Pages 602–607, 1978; Ionescu, M. I. et al., LONG-TERM CLINICAL AND HAEMODYNAMIC EVALUATION OF THE IONESCU-SHILEY PERICARDIAL XENOGRAFT HEART VALVE, Thoraxchirurgie, Volume 26, Pages 250–258, 1978; Ionescu, M. I. et al., LONG-TERM SEQUENTIAL HEMODYNAMIC EVALUATION OF RIGHT VENTRICULAR OUTFLOW TRACT RECONSTRUCTION USING A VALVE MECHANISM, The Annals of Thoracic Surgery, Volume 27, No. 5, May, 1979; Ross, D. N., FLEXIBLE BIOPROSTHETIC PERICARDIAL HEART VALVE, Thoracic & Cardiovascular Surgery, Volume 28, Pages 150–152, 1980.

Particular techniques for preparing, handling and storing tissue valves are disclosed in U.S. Pat. Nos. 3,966,401, Hancock et al., June 29, 1976, and 4,182,446, Penny, January, 1980.

Some of the earliest heart valve prostheses were flexible two- or three-cusp valves in which the cusps were constructed on various types of fabric. Some of these flexible leaflet valves had good flow characteristics but most failed. The leaflets tore, separated from the annulus, or became rigid due to fibrous tissue ingrowth. From about 1960 into the 1970's, the trend was to mechanical valves. These ranged from the mechanically quite simple Starr-Edwards valve to the relatively sophisticated Bjork-Shiley valve and included a number of disc poppet valves. These mechanical valves generally dominated the market notwithstanding limitations on haemodynamic performance and are still very satisfactory for many applications. In 1962, Donald Ross and Sir Brian Barratt-Boyes, independently, were performing implantations of homograft tissue valves some of which were free graft implants and some of which were mounted on supporting stents. Fully clothed covered rigid stents were used in some of these homograft valves.

In 1965, Drs. Binet and Carpentier, and their associates, implanted a specially prepared porcine aortic valve xenograft. These porcine valves were sterilized and treated, e.g. with formaldehyde, and were commonly attached to a metal stent. Experience showed that these valves were of short life, largely because of the heterograft nature of the valve tissue. Dr. Carpentier, in about 1968, established the concept of the bioprosthesis by substantially eliminating antigenicity of the tissue, principally by changing the preservative from formaldehyde to glutaraldehyde. A number of porcine bioprostheses and specially designed stents for supporting these prostheses resulted from the efforts of Warren Hancock et al. Generally, pig aortic valves are procured under clean conditions, placed in a cold, balanced electrolyte solution, excess tissue is trimmed and the xenografts are immersed in 0.2% glutaraldehyde. The leaflets are held in their normal valving position under pressure during the tanning process and each valve is sutured to a cloth covered stent by multiple rolls of interrupted and continuous suture. A number of designs and stent constructions for the Hancock type valve are exemplified in the aforementioned U.S. Pat. Nos. 3,570,014; 3,755,823, for example. Stents for porcine valves were developed by a number of other workers also, see, e.g., U.S. Pat. Nos. 3,983,581; 4,035,849; 4,079,468 and 4,106,129.

Stents for supporting cusp valves of other tissue members, e.g. fascia lata and pericardium, have been developed by a number of workers, see, e.g., U.S. Pat. No. 3,714,671, and Edwards et al., MITRAL AND AORTIC VALVE REPLACEMENT WITH FASCIA LATA ON A FRAME, supra. Much of the pioneering work in this area of valve development was done by Dr. Marian I. Ionescu and his associates, see, e.g., Bartek, et al., FRAME-MOUNTED TISSUE HEART VALVES: TECHNIQUE OF CONSTRUCTION, Thorax, Volume 29, Pages 51–55, 1974; Ionescu, et al., HEART VALVE REPLACEMENT WITH IONESCU-SHILEY PERICARDIAL XENOGRAFT, Cardiology Digest, June, 1977; Ionescu, et al., HEART VALVE REPLACEMENT WITH IONESCU-SHI- LEY PERICARDIAL XENOGRAFT, The Journal of Thoracic and Cardiovascular Surgery, Volume 73, Pages 31–42, 1977; Tandon, et al., LONG-TERM HAEMODYNAMIC EVALUATION OF AORTIC PERICARDIAL XENOGRAFT, British Heart Journal, Volume 40, Pages 602–607, 1978; Ionescu, et al., LONG-TERM CLINICAL AND HAEMODYNAMIC EVALUATION OF THE IONESCU-SHILEY PERICARDIAL XENOGRAFT HEART VALVE, Thoraxchirurgie, Volume 26, Pages 250–258, 1978; Ionescu, et al., LONG-TERM SEQUENTIAL HEMODYNAMIC EVALUATION OF RIGHT VENTRICULAR OUTFLOW TRACT RECONSTRUCTION USING A VALVE MECHANISM, The Annals of Thoracic Surgery, 27, 425–434, 1979; and Ionescu, Editor, TISSUE HEART VALVES, Butterworths, 1979.

A number of improvements in the basic Ionescu tissue heart valve have been made. For example, a tissue heart valve has been developed which has a cloth-covered stent of special construction, in which the outflow annulus diameter of the valve is defined and limited by the positioning of a coaptation stitch on the inside of the supporting legs of the stent, as has been the practice since the early development of the Ionescu type tissue heart valve. Another improvement in the method for aligning the tissue of the cusps of the Ionescu type heart valve is described in U.S. Pat. No. 4,172,295 which also disclosed the coaptation stitch inside the stent legs. It has been the practice, in order to achieve a maximum flow orifice in valves of implantation diameters less than or equal to 23 mm, to splay the stent legs outwardly in an effort to achieve a full-flow orifice inside the captation stitches.

While these various modifications and improvements in the basic Ionescu valve over the years have solved some of the problems, there remain a number of problems which have not been solved. Among these problems are the limitations on the size of the flow annulus which can be obtained, with consequent increased pressure gradient across the valve. Perhaps the most important disadvantage of the three-cusp tissue valves of the prior art is the fact that in each cusp there are two points of stress due to three-dimensional flexure at about 4 o'clock and at about 8 o'clock in the lower arc of the cusp, i.e. in the lower right hand portion and the lower left hand portion of the closed cusp as viewed laterally, head-on, from the outside. A similar phenomena is created by creases which tend to concentrate stress in the areas of the crease.

The tissue valves of the prior art generally have relied upon a face-to-face meeting of the cusps in the closed position and, consequently, have required relatively high stent legs and in general the tissue valves of the prior art have trimmed the tissue around the outflow end so as to form a generally round regular cylindrical configuration. This approach has resulted in the concentration of stresses in fold areas or in the lower right and left hand portions of the cusps.

These problems are largely or entirely solved by the present invention.

DISCLOSURE OF THE INVENTION

The present invention comprises an improved tissue valve prosthesis of the Ionescu type. The improved prosthetic heart valve of this invention comprises a stent which includes an annular base integrally formed with three legs which extend upwardly a distance U from the lowermost portion of a scallop on the base to the outflow ends of the legs. The space between the legs is configured to form generally elliptically shaped scallops having a depth U measured from the top of the post to the bottom of the scallop. The stent, circumferentially, forms a right cylinder having a uniform inside diameter $D_{in}$, where $D_{in}$ means the inside diameter of the stent at the inflow end, the legs extending parallel to the axis of the right cylinder. The lower edge of the stent forms scallops which correspond generally to the arc of the scallops between the legs. The scallops of the lower edge of the base and the scallops between the legs vertically define three generally elliptically shaped one-third portions of the base between their respective upright legs. A fabric covering totally encompasses and follows the configuration of the stent and an annular sewing ring is attached to the fabric covering and extends outwardly from the base. A tissue valve element is formed of three tissue leaflets, joined to form a generally cylindrical three-cusp valving element, each of the leaflets having a top edge forming a truncated triangle with a central high plateau tapering down on each side of the plateau to the corners adjacent the sides of the leaflet, giving the top of each leaflet a generally very obtuse, flat topped generally truncated triangular configuration. Conventional stitching or other means are provided and attach the tissue valve element around the fabric covered stent to the fabric, around the annulus formed by the stent and up the outside surface of the fabric covered stent legs. A coaptation stitch through the tissue leaflets adjacent the upper edge thereof, and disposed directly above the top of the fabric covered stent, fixes the leaflets in position to form three cusps each having an upwardly extending point, extending in the outflow direction, midway between the legs. The upper edges, or outflow edges, of the cusps meet, in the closed position of the valve, with the points adjacent each other. In the open position, the tissue valve element forms a cylinder having an inside diameter at the top of the valve substantially equal to the inside of the diameter of the fabric covered stent, the flow path through the valve generally being in the configuration of a right cylinder with the axis of the cylinder corresponding to the flow axis of the valve, the legs and the stents forming a circumferentially right cylindrical surface around the axis, with the suture or sewing ring forming an annulus around the stent.

For convenience, in describing the valve, the outflow end of the valve is depicted at the top of the drawings and the valve is described in this configuration; thus, the upward or top portion of the valve would correspond to the outflow portion of the valve and the bottom would correspond to the inflow end of the valve.

In the prosthetic valve of this invention, the scallop depth U of the stent is between 50% and 65% of the stent diameter $D_{in}$, the inside diameter of the stent at the inflow end. Optimally, the stent scallop depth U is from about 55% to about 62% of the diameter $D_{in}$. This $U/D_{in}$ ratio is very important in providing a low profile tissue valve prosthesis which has optimum flexure and coaptation of the leaflets using tissue fixed in the unstressed state. These factors result in an increased valve life.

The outflow end of the three cusps of the valving member are, in the closed position, adjacent in the center and in face-to-face contact with each other along radii defined by the legs. The upper or outflow ends of the valving element lie in substantially face-to-face contact between the interior faces of the cusps of the valving element with from 0 to 1 or 2 mm depth of coaptation in the center of the valving element and from 3 to 7 mm depth of coaptation intermediate the center of the valve and the legs, along the radial contact lines.

BRIEF DESCRIPTION OF THE DRAWINGS

FIG. 1 is a perspective view of the valve of this invention.

FIG. 2 is a top and side view of the stent which forms a significant part of the invention, including the significant points of measurement of the stent.

FIG. 3 is a prior art stent, utilized in one of the improvements of the basic Ionescu valve, and showing the basic measurements thereof for purposes of comparison with the present invention.

FIG. 4 is a perspective view of the stent of the inventive valve.

FIG. 5 is a flat plan view of the outline of one of the leaflets used in the present valving member, before the sewing of three such leaflets together to form a cylindrical valving member.

FIG. 6 is an exploded view of the cloth covered stent and valving member of the invention showing the relationship and structure thereof immediately before attaching the tissue valving member to the stent.

FIG. 7 is a perspective detail showing the attachment of the tissue to the stent. FIG. 8 is a perspective view showing the finishing of the valve of the present invention.

FIG. 9 is a partial cross-section taken along lines 9—9 of FIG. 8 showing the closed cusps of the valve leaflets along the closure line.

FIG. 10 is a top plan view, viewed from the outflow end, of the valve of this invention showing the valve in full open position.

FIG. 11 is a top plan view, viewed from the outflow end of the valve, showing the valve of this invention in full closed position.

As depicted in FIG. 1, the present invention is a low profile pericardial xenograft heart valve 10 which comprises a valving element 20, a stent assembly 100 and a suture or sewing ring assembly 200, shown in FIGS. 1, 4 and 6.

The upper portion of FIG. 6, depicts the valving element 20, showing generally the three stitch seams 22, 24 and 26 which join the three leaflets 30, 50 and 70 into a cylindrical valving element which is then fitted over the stent assembly 100.

FIG. 5 depicts one of the leaflets of the valving element 20, as exemplary of all of the leaflets 30, 50 and 70, all of which are substantially identical. The leaflet 30 of FIG. 5 is a generally flat layer or sheet of pericardium tissue, treated as will be described and discussed in more detail hereinafter, and includes a curved bottom 32 and curved sides 34 and 36 with a top, or outflow edge generally indicated at 40. The top 40, however, comprises three distinct portions, edges 42 and 44 which converge upwardly, like symmetrical sides of a triangle to a central plateau 46 at the top, and forming obtuse corners with the sides 34 and 36, respectively, on the bottom. Each of the leaflets 30, 50 and 70 are to be understood as including corresponding elements, including the top or outflow edge 60 and 80, as shown in FIG. 6, for example, and plateaus 66 and 86 corresponding to plateau 46. The three leaflets 30, 50 and 70 are in all essential respects identical, although there will be some minor variation in the exact shape and size of these leaflets because they are made from naturally occurring tissue and considerable manual dexterity and skill is required in production. Minor variations, so long as the function is not impaired, are readily tolerated in the present valve construction.

The shape of the leaflets 30, 50 and 70 is very important to the proper functioning of the valve. However, precise dimensions are not critical because minor deviations and dimensions can be compensated for in the final joinder of the leaflets into the valving element and in fitting the valving element over the stent. One portion of the configuration of the leaflets is of vital importance to the optimum functioning of the present invention, although the invention will function in an improved manner over the prior art even if very minor deviations are permitted. This important configuration is the truncated triangular top edge converging to the plateau 46 in FIG. 5 and plateaus 66 and 86 in the leaflets 50 and 70. The base of the triangle is, of course, an imaginary line joining the lower corners of the top edge. Plateau 46 is centrally located between the juncture of the outflow edge portion 42 with side 34 and outflow edge portion 44 with side 36. The best definition of the shape of this obtuse truncated triangle defined by the plateau 46 and the juncture of the top edges 42 and 44 with the sides of the leaflet, is that this truncated triangle is so configured and dimensioned that when the three leaflets are sewn together at their respective edges to form a cylinder, and fitted over a stent, with a coaptation stitch positioned directly over the end of the stent when the valve is closed, the center 46 of the leaflet 30 touches, or substantially touches, the corresponding centers 66 and 86 of the leaflets 50 and 70, with no more than about 1 mm of face-to-face contact, in the center of the flow path of the valve with substantial face-to-face contact, i.e. from about 2 mm to about 6 or 7 mm, between the interior surfaces of the edges intermediate the center and the outer diameter of the valve. Exactitude is not required, but it is required that the plateaus 46, 66 and 86 be in touching or substantially in touching relationship when the valve is closed, and that there be substantial surface-to-surface contact along the central portion of the radial coaptation lines of cusp contact. This relationship is shown in FIG. 9 which depicts the valve of FIG. 1 cut parallel to a radii defined by the cusp coaptation line, the area of contact being shown. The maximum face-to-face contact is about halfway between the center and the legs and would be at least 2 or 3 mm but not more than 9 or 10 mm. Optimally the area of coaptation should be from 3 to 7 mm at a point midway between the center of the valve element and the stent leg depending on valve size.

It is neither necessary nor possible to give exact shape and dimensional definitions to the leaflets exemplified by leaflet 30, but the configuration may be described, realizing that the truly critical relationship is the interrelationship of the three obtuse truncated triangular portions. The maximum width of the leaflets lies about the midpoint thereof. The height of the leaflet is, of course, of no criticality whatever, however, and so this is merely a general relationship. Thus, the sum of Sa, Sb, and Sc, is approximately equal to one-half of the total vertical height of the leaflet, Sa representing the mean altitude of the obtuse truncated triangle formed by plateau 46 and the converging edge portions 42 and 44 and the base formed by the juncture between top edge with side 34 and side 36 respectively, Sb plus Sa being equal to about 35% plus or minus 3 to 5% of the total height and the sum of Sa, Sb and Sc being about 50% plus or minus around 10% of the total vertical height. The width of the leaflet Wa, measured Sa down from the point 46 is about 85% plus or minus 10% of the maximum width of the leaflet, Sa being around 12 to 17% of the total height. The width Wb measured at Sa plus Sb from the point 46 is about 95% plus or minus about 5% of the maximum width. Sa plus Sb is about 30 to 40%, generally around 35% of the total height. The maximum width is usually at about 45 to 55% of height. The exact width and height ratios depends upon the overall size of the valve and generally will fall within the ranges indicated, although the first definition by function is the best and most meaningful description presently comprehended. In a specific embodiment, the valving member for the size 23 valve is a section of pericardium 0.012 inch thick, with a maximum height of 21 millimeters, a maximum width Wc of 26.5 millimeters at about 52% of total height, the width Wa of the obtuse triangle is 22.5 millimeters measured at Sa down about 14% of the total height from the top, the intermediate width Wb being 25.5 millimeters at Sb, 35% from the top. Again, this is merely one example of one size of a valve and the dimensions are not the critical factor, it is the interrelationship of the top edges of the leaflet which are critical.

Glutaraldehyde has been used effectively to stabilize connective tissue for clinical heart valve substitutes for several years. The tissue leaflets of the present invention are cut from pericardium tissue, although other tissues may be used. The use of formaldehyde and glutaraldehyde tanning in preservation of tissue is described by E. Aubrey Woodruff, *The Chemistry and Biology of Aldehyde Treated Tissue Heart Valve Xenografts*, in Ionescu, TISSUE HEART VALVES, Butterworths, 1979, and other contributors to TISSUE HEART VALVES, discuss in detail the glutaraldehyde tanning and preservation of connective tissue. This disclosure is incorporated herein by reference. In the preferred embodiment of the present invention, pericardium treated with 0.5% glutaraldehyde at pH 7.4 without fixing the tissue in a prestressed condition is preferred; however, it is to be understood that the invention disclosed and claimed here relates to the configuration of the valving leaflets and member and the supporting stent, and any suitably preserved tissue may be utilized in the present invention.

The stent assembly 100 refers generally to the entire stent assembly which includes a biologically compatible metal or plastic stent 102. The stent 102 defines the configuration of the stent assembly 100. The stent 102 may be considered as three one-third portions of a stent integrally formed of one piece of material although, of course, the method of formation or the number of pieces is of no consequence provided the end stent is as described herein. The stent 102 comprises a base or ring 104 which extends around and defines the flow orifice of the valve. Extending upwardly, as depicted in the figures, or toward the outflow end of the valve considering the functional inflow and outflow ends of the valve, are three substantially identical legs 106, 108 and 110 each separated by a scallop 112 between legs 106 and 108, 114 between legs 108 and 110, and 116 between legs 106 and 110. The bottom or inflow edge of the stent 102 is also in a scalloped configuration, the scallops of the inflow edge generally following the configuration of the scallops of the outflow edge, but, of course, not being nearly so deep, the scallops extending in the outflow direction from the inflow direction underneath each of the respective legs 106, 108 and 110. The scallops of the lower or inflow edge of the base and the scallops of the outflow edge between the legs vertically define three generally elliptical shaped one-third portions of the base between the respective upright legs.

The stent assembly 100, in the preferred embodiment, also includes a fabric which totally or at least substantially encloses the stent 102. It is not essential to the functioning of the present valve that the stent be cloth-covered but it has been long recognized that there are structural and biological advantages to a fully cloth-covered valve and, in particular, to the use of fully cloth-covered stents for supporting tissue valves. This concept, of course, predates the present invention and constitutes no part thereof but is simply adopted as part of the best mode in carrying out the present invention. The fabric covering described in detail by Ionescu et al. in U.S. Pat. No. 4,084,268, Apr. 18, 1978, has been generally adopted and the same techniques are applied in the present invention as are applied in the Ionescu et al. type cloth-covered prosthetic tissue heart valve stent. Reference is made to U.S. Pat. No. 4,084,268 for specific details of the fabrics, knots, sewing and techniques. It is sufficient here to describe the stent assembly as including a cloth covering which encloses or substantially encloses and conforms to the stent.

FIG. 7 is a cut away and partial cross-section depicts a fabric 120 enclosing the outside of the stent, a fabric 122 which encloses the inside of the stent, with a suitable seam area 124 joining the fabrics along the top or outflow edge of the stent, and a fabric 126 joined along the lower edge of the stent and extending outwardly forming part of and attaching a sewing or suture ring generally indicated at 200 which may be of any of the forms used in the prior art. Generally, such suture rings comprise a plurality of layers of fabric and padding, 202, 204 and 206, enclosed in layer 126, soft enough to permit the suturing needle to be readily inserted through it and yet rigid and strong enough to provide firm mounting of the prosthesis into the heart valve area. The suture ring 200 of this invention differs from the prior art suture rings only in that it curves and conforms to the scalloped contour of the valve ring or base defined by the portion 104 of the stent 102. The tissue leaflets, after being sewn to form a cylinder, may be sewn to the stent assembly in any conventional manner, as, for example, by running stitches shown at 210.

FIG. 7 depicts the valve in partially completed configuration with the tissue leaflets 30 and 70 joined by seam 22, the upper edges 80 and 40 substantially touching or just touching, without a large or significant surface-to-surface touching of the two leaflets.

FIG. 8 shows the completion of the valve shown in FIG. 7 by the addition of the pledget and cover 220 which is sewn by stitches 222 to the posts through the tissue, all as described by Ionescu et al. in U.S. Pat. No. 4,084,268, or in any other convenient manner. The inclusion of the fabric covering, the pledget, the sewing as described, etc., all as disclosed with great particularity by Ionescu et al., supra, are utilized in carrying out the invention in its preferred embodiment, but, per se, are not part of the invention.

As best shown in FIG. 7, the present invention departs in a very important and very significant manner in the way in which the coaptation of the edges 40 and 60, the edges 40 and 80 and the edges 60 and 80 abut in touching relationship. This coaptation is defined, in significant part by the placement of the coaptation stitches 130, 132, and 134, directly above the respective stent legs 106, 108 and 110, the placement of the coaptation stitch 130 being depicted in FIGS. 7 and 8.

Another extremely significant departure from the prior art, taken in combination with the subject matter as a whole, is the relative height H of the stent 102, the depth U of the scallops between the legs of the stent 102, and the diameter Din of the stent.

In the prior art, it was considered necessary, or at least very important, that in smaller valve sizes, e.g. 23 mm or less, the legs be splayed outwardly from the base. Thus, referring to FIG. 3, in the prior art stent 102', the input diameter Din was smaller than the outflow diameter Dout, Dout being the diameter of the circle in which the legs at the outflow end of the valve lie. The coaptation stitches of the prior art performed inside the legs and the circle on which these coaptation stitches was made to lie was made, or attempted to be made, approximately equal to Din. Thus, the stent, viewed circumferentially, e.g. from the end, was not a right cylinder, but was generally frustoconical because of the splaying. Sometimes, of course, the splaying of the legs was accomplished by bending the legs out from another wide cylindrical base, but the result was substantially the same as a frustoconical imaginary figure derived from the diameter of the inflow and the outflow ends of the valve.

In contrast to the prior art, the stent 102 of the present invention is, viewed circumferentially, a right cylinder, the axis of the cylinder lying in the center of the path, the legs extending from the inflow toward the outflow end of the valve, the top as viewed in the figures, parallel to the axis of the right cylinder. Thus, Din became equal to Dout, as depicted in FIG. 2.

Also of great significance is the ratio U/Din Din being equal, of course, to Do. As compared with what is regarded as the closest and most pertinent prior art, the Ionescu type valve described by Ionescu et al. in U.S. Pat. No. 4,084,268, various features of which are also described in U.S. Pat. No. 4,172,295 to Batten, the scallop depth U measured from the upper edge of the scallop bottom on the outflow end of the stent to the upper or outflow end of the legs, is very much less than the corresponding distance of the prior art stent as depicted in FIG. 3, for a given valve diameter. In particular, the ratio of U/Din in the present valve is between about 0.50 and about 0.65, and optimally from about 0.55 to 0.62.

It is important, of course, to obtain and maintain as low a profile valve as can be made to operate; but that alone is not the only significance of the aforesaid ratio of U/Din. This result, long sought for but heretofore unattainable, is obtained by reason of the unique combination of elements, configurations, relationships, and dimensional ratios, which, acting together in a unique way, and make it possible to provide a heart valve prosthesis, in which the valving element is a generally cylindrical tissue element, which has a profile of less than two-thirds the profile of prior art valves, which closes more rapidly than prior art valves of related construction, and in which the stresses in the cusps found in prior art valves have been wholly or substantially avoided. This new result comes about by reason of the interaction between the U/Din ratio of the stent, the positioning of the coaptation stitch above the end of the stent leg, and the unique configuration of the cusp leaflets of the valving member.

As will be seen in FIG. 10, when the valve is in the full open position, the flow path is substantially a right cylinder, through the valve, the coaptation stitch is placed directly above the leg. This has two functions. The first is of significance but, comparatively, of lesser significance than the other. The first result of this placement of the coaptation stitch is that a larger flow orifice is obtained without the necessity for splaying the legs of the valve. More importantly, the stresses of the prior art tissue valves at four o'clock and at eight o'clock, i.e. the lower right and the left-hand portions of the cusp, when viewing the cusp straight on laterally, have been avoided without fluttering, rolling and floating of the edge of the tissue, at the outflow end of the valve. This is a new and extremely desirable result which flows from the combination of configurations described. This result is accomplished by reason of the unique configuration of the leaflets in which the valve element comprises three tissue leaflets joined to form a generally cylindrical valve element having three points which extend centrally of each of the cusps respectively toward the outflow end of the valve, centrally between ends of the legs, the valve element forming in the open position a cylinder having three points on the outflow end thereof and, in the closed position, forming three cusps which arc inwardly between the legs, the outflow end of the leaflets touching with the three points adjacent each other in the center of the outflow end of the valve. It will be apparent from a consideration of the structure of the leaflets that, while in the preferred embodiment they are formed of three separate pieces, they may very well be formed of a single integral piece of tissue with appropriate cutting and stitching such that the end result, the valving element, has the proper configuration. Thus, while it is convenient to start with three pieces of tissue, the same invention may be practiced with only one piece in which the three leaflets are integrally joined.

The shortening of the implant depth, to less than about two-thirds of the prior art stent heights of corresponding valves, and the adoption of the coaptation stitch directly above the ends of the legs, permit the use of the aforesaid described valving element while providing a substantial area of face-to-face overlapping contact along the radial contact lines of the cusps and obviating the tendency of the outflow end of the leaflets to roll, flutter, and otherwise to delay in closing or to twist and deform by minimizing the coaptation, at the center of the valve, of the plateaus 46, 66 and 86.

As exemplary only and not in any limiting sense, current optimum stent dimensions are given in Table I. The "outside diameter" referred to in the second column from the left is the outside diameter of the stent at either the inflow end or the outflow end in FIG. 2 since the stent 102 is of a right cylindrical configuration.

TABLE I

STENT DIMENSIONS (mm)

| Nominal Valve Size | Outside Diameter | Inside Diameter | Height | Scallop Thickness | "U" Scallop Depth | Insertion Depth | Post Top Width | "U"/"D" in |
|---|---|---|---|---|---|---|---|---|
| 15 | 13.52 | 12.76 | 9 | 2.03 | 7.87 | 4.72 | 1.778 | .62 |
| 17 | 15.94 | 14.73 | 10.16 | 2.03 | 8.89 | 5.33 | 1.778 | .60 |
| 19 | 17.53 | 16.76 | 11.18 | 2.03 | 9.65 | 5.97 | 1.778 | .58 |
| 21 | 19.56 | 18.80 | 12.45 | 2.29 | 10.67 | 6.60 | 2.032 | .57 |
| 23 | 21.34 | 20.57 | 13.5 | 2.29 | 11.68 | 7.24 | 2.032 | .56 |
| 25 | 23.37 | 22.60 | 14.73 | 2.54 | 12.7 | 7.87 | 2.032 | .56 |
| 27 | 25.40 | 24.64 | 15.88 | 2.54 | 13.72 | 8.50 | 2.032 | .56 |
| 29 | 27.31 | 26.54 | 17.07 | 2.54 | 14.73 | 9.14 | 2.032 | .56 |
| 31 | 29.51 | 28.75 | 18.24 | 2.54 | 15.95 | 9.78 | 2.032 | .55 |
| 33 | 31.25 | 30.43 | 20.11 | 2.79 | 17.06 | 10.39 | 2.032 | .56 |

It will be apparent by now that a new result not heretofore attainable has been accomplished in a new way using new concepts and design criteria and new structures and new structural and functional relationships not heretofore contemplated and which work together in a unique operation and function not before considered.

It will also be apparent that the foregoing description, given in considerable detail as to the method of carrying out the best mode of the invention as contemplated by the inventor, is given to exemplify the concepts and principles of the invention and not to limit it. The stent may be made of titanium, Delrin (TM) polyacetal or Elgiloy with the fabric covering of Dacron and Teflon but the invention is not limited to these materials nor is it limited to any particular covered stent; indeed, the present invention can be carried out without a covered stent. Similarly, the structures and elements of the invention have been described, in their exemplary, best mode, embodiments, as either integral, in the case of the stent, or separate, in the case of the leaflets, but, of course, whether integral or separate, whether formed of one or many pieces, if the structure which results functions in the manner described, it is the same invention. Thus, it is contemplated that the scope of the invention will be as defined in the following claims read in light of the principles of the invention as disclosed herein and not limited by the best mode which has been described in considerable detail.

INDUSTRIAL APPLICATION

The present invention will find the great application in the manufacture of heart valve prostheses in the medical and surgical profession.

What is claimed is:

1. A prosthetic heart valve comprising:
a stent comprising an annular base integrally formed with three legs extending upwardly a distance H from the lowermost portion of the base, the space between the legs configured to form generally elliptically shaped scallops having a depth U measured from the top of the posts to the bottom of the scallop, the stent circumferentially forming a substantially right cylinder having an interior diameter D with the legs extending parallel to the axis of the cylinder, to the lower edge of the stent forming scallops corresponding generally to the arc of the scallops between the legs, the scallops of the lower edge of the base and the scallops between the legs vertically defining three generally elliptically shaped one-third portions of the base between the respective upright legs;

fabric covering totally encompassing and following the configuration of the stent;
an annular sewing ring attached to the fabric covering, extending outwardly from the base;
a tissue valve element formed of three tissue leaflets joined to form a generally cylindrical three-cusp valving element, each leaflet having a top edge forming a raised truncated triangular form with a central plateau, the sides diverging from each side of the plateau to corners adjacent sides of the leaflet;
means attaching the tissue valve element around the fabric covered stent; and
a coaptation stitch through the tissue leaflets adjacent the upper edge thereof disposed directly above the top of the fabric covered stent legs fixing the leaflets to form three cusps with said plateau extended upwardly midway between the legs, the upper edges of the cusps meeting in the closed position of the valve with the plateaus adjacent each other, and in the open position of the valve the tissue valve element forming a cylinder having an inside diameter at the top of the valve substantially equal to the inside diameter of the fabric covered stent.

2. The prosthetic heart valve of claim 1 wherein the ratio U/D is from 0.5 to 0.65.

3. The prosthetic heart valve of claim 2 wherein the ratio U/D is from about 0.55 to about 0.62.

4. The prosthetic heart valve of claim 3 wherein the width of the area of coaptation of the cusps in the closed position is about 0 to 1 mm in the center and about 3 to 7 mm halfway between the center of the valve and the coaptation stitch.

5. The prosthetic heart valve of claim 1 wherein the sewing ring extends outwardly circumferentially forming an annulus vertically following the scalloped curvature of the base of the stent.

6. The prosthetic heart valve of claim 5 wherein the ratio U/D is from about 0.50 to about 0.65.

7. The prosthetic heart valve of claim 6 wherein the ratio U/D is from about 0.55 to about 0.62.

8. In a xenograft heart valve prosthesis which comprises a circumferentially annular stent having an annular base and legs extending vertically from the base toward the outflow end of the valve, a sewing ring circumferentially attached annularly to the outside of the stent, and a three-cusp tissue valve element attached to the stent, the improvement wherein the valve element comprises three tissue leaflets joined to form a generally cylindrical valve element having three truncated triangular portions extending centrally of each of the cusps respectively toward the outflow end of the valve each having a plateau centrally between the legs extending in the outflow direction of the valve beyond the ends of the legs, the valve element forming in the open position a cylinder having three truncated triangles on the outflow end thereof and in the closed position three cusps arcing inwardly between the legs, the outflow end of the leaflets touching with the three plateaus adjacent each other in the center of the outflow end of the valve.

9. The prosthesis of claim 8 wherein the cusps of the valve lay in face-to-face contact along a radial line from the legs to the center, the width of the contact being from 0 to 2 mm in the center of the valve and from about 3 to about 7 mm about halfway between the center and the leg of the stent.

10. The prosthesis of claim 8 wherein the stent circumferentially is in the form of a right cylinder of constant diameter.

11. The prosthesis of claim 8 wherein the distance U from the inflow end of the stent to the bottom of the scallop on the outflow end of the stent is from about 0.50 to about 0.62 of the inside diameter of the stent.

12. In a xenograft heart valve prosthesis which comprises a circumferentially annular stent having an inflow end and an outflow end, the stent including an annular base and legs extending in the outflow direction therefrom, three outflow end scallops, an annular sewing ring attached to and surrounding the stent, and a tissue valving member around and attached to the stent to form a three-cusp valve, the cusps being located, respectively, in the scallops between the respective three legs, the improvement wherein the depth U of the scallops, as measured from the bottom of scallops on the outflow edge of the stent to the outflow end of the legs, is from 0.50 to about 0.65 of the internal diameter D of the stent and wherein said valving member is formed to have three truncated triangular portions converging to three plateaus.

13. The prosthesis of claim 12 wherein the stent is circumferentially a right cylinder of constant diameter measured at both the inflow and outflow ends thereof.

14. In a xenograft heart valve prosthesis which comprises a circumferentially annular stent having an inflow end and an outflow end, the stent including an annular base and legs extending in the outflow direction therefrom, three outflow end scallops, an annular sewing ring attached to and surrounding the stent, and a tissue valving member around and attached to the stent to form a three-cusp valve, the cusps being located, respectively, in the scallops between the respective three legs, the improvement wherein the depth U of the scallops as measured from the bottom of scallops on the outflow edge of the stent to the outflow end of the legs, is from 0.50 to about 0.65 of the internal diameter D of the stent and wherein said stent is circumferentially a right cylinder of constant diameter measured at both the inflow and outflow ends thereof and wherein the tissue valving member is generally cylindrical in form and is formed to have three truncated triangular portions extending from the outflow end thereof intermediate between the legs forming three plateaus which lie adjacent each other when the valve is closed.

15. The prosthesis of claim 14 further comprising fabric enclosing and conforming to the stent, the sewing ring and the valving member being attached to the fabric.

16. The prosthesis of claim 12, 13, 14 or 15 wherein U is from about 0.55 to about 0.62 of D.

17. The prosthesis of claim 12, 13, 14 or 15 wherein the cusps of the valve lay in face-to-face contact along a radial line from the legs to the center, the width of the contact being from 0 to 2 mm in the center of the valve and from about 3 to about 7 mm about halfway between the center and the leg of the stent.

18. In a xenograft heart valve prosthesis which comprises a circumferentially annular stent having an annular base and legs extending vertically from the base toward the outflow end of the valve, a sewing ring circumferentially attached annularly to the outside of the stent, and a three-cusp tissue valve element attached to the stent, the improvement wherein the valve element comprises a generally cylindrical tissue valve element having an inflow end and an outflow end, the outflow end of the valve element comprising three substantially equal portions, each of said portions having a truncated triangular edge forming a central plateau edge which extends centrally of such portion toward the outflow end of the valve, being positioned intermediate the legs of the stent, the valve element forming in the open position a cylinder with three plateaus on the outflow end thereof and in the closed position three cusps arcing inwardly between the legs, the outflow ends of the leaflets touching each other, the three plateaus adjacent each other in the center of the outflow end of the valve.

19. The prosthesis of claim 18 wherein the cusps of the valve lay in face-to-face contact along a radial line from the legs to the center, the width of the contact being from 0 to 2 mm in the center of the valve and from about 3 to about 7 mm about halfway between the center and the leg of the stent.

20. The prosthesis of claim 18 further comprising a coaptation stitch adjacent the top of each leg and wherein the width of the area of coaptation of the cusps in the closed position is about 0 to 1 mm in the center and about 3 to 7 mm halfway between the center of the valve and the coaptation stitch.

21. In a xenograft heart valve prosthesis which comprises a circumferentially annular stent having an inflow end and an outlfow end, the stent including an annular base and legs extending in the outflow direction therefrom, three outflow and scallops, an annular sewing ring attached to and surrounding the stent, and a tissue valving member around and attached to the stent to form a three-cusp valve, the cusps being located, respectively, in the scallops between the respective three legs, the improvement wherein the depth U of the scallops, as measured from the bottom of scallops on the outflow edge of the stent to the outflow end of the legs, is from 0.50 to about 0.65 of the inside diameter $D_{in}$ of the stent; the stent is circumferentially measured at both the inflow and outflow ends thereof, the cusps of the valve being in face-to-face contact along a radial line from the legs to the center, the width of the contact being from 0 to 2 mm in the center of the valve and from about 3 to about 7 mm about halfway between the center and the leg of the stent.

22. In a xenograft heart valve prosthesis which comprises a circumferentially annular stent having an inflow end and an outflow end, the stent including an annular base and legs extending in the outflow direction therefrom, outflow end scallops, an annular sewing ring attached to and surrounding the stent, and a tissue valving member attached to the stent to form valve cusps, the cusps being located, respectively, in the scallops between the respective legs of the stent, the improvement wherein tissue cusps are formed of tissue fixed in the unstressed state, and wherein:

said stent comprises an annular base integrally formed with three legs extending upwardly a distance H from the lowermost portion of the base, the space between the legs configured to form generally elliptically shaped scallops having a depth U measured from the top of the posts to the bottom of the scallop, the stent circumferentially forming a substantially right cylinder having an interior diameter D with the legs extending parallel to the axis of the cylinder, to the lower edge of the stent forming scallops corresponding generally to the arc of the scallops between the legs, the scallops of the lower edge of the base and the scallops between the legs vertically defining three generally elliptically shaped one-third portions of the base between the respective upright legs;

including fabric covering totally encompassing and following the configuration of the stent;

the annular sewing ring being attached to the fabric covering, extending outwardly from the base;

the tissue valving member being formed of three tissue leaflets joined to form a generally cylindrical three-cusp valving element, each leaflet having a top edge forming a raised truncated triangular form with a central plateu, the sides diverging from each side of the plateau to corners adjacent to sides of the leaflet;

including means attaching the tissue valve element around the fabric covered stent; and also including a coaptation stitch through the tissue leaflets adjacent the upper edge thereof disposed directly above the top of the fabric covered stent legs fixing the leaflets to form three cusps with said plateau extended upwardly midway between the legs, the upper edges of the cusps meeting in the closed position of the valve with the plateaus adjacent each other, and in the open position of the valve the tissue valve element forming a cylinder having an inside diameter at the top of the valve substantially equal to the inside diameter of the fabric covered stent.

23. The prosthetic heart valve of claim 22 wherein the ratio U/D is from 0.5 to 0.65.

24. The prosthetic heart valve of claim 22 wherein the ratio U/D is from about 0.55 to about 0.62.

25. The prosthetic heart valve of claim 22 wherein the width of the area of coaptation of the cusps in the closed position is about 0 to 1 mm in the center and about 3 to 7 mm halfway between the center of the valve and the coaptation stitch.

26. In a xenograft heart valve prosthesis which comprises a circumferentially annular stent having an inflow end and an outflow end, the stent including an annular base and legs extending in the outflow direction therefrom, outflow end scallops, an annular sewing ring attached to and surrounding the stent, and a tissue valving member attached to the stent to form valve cusps, the cusps being located, respectively, in the scallops between the respective legs of the stent, the valving member comprising three tissue lejaflets joined to form a generally cylindrical valve element having three truncated triangular portions extending centrally of each of the cusps respectively toward the outflow end of the valve each having a plateau centrally between the legs extending in the outflow direction of the valve beyond the ends of the legs, the valve element forming in the open position a cylinder having three truncated triangles on the outflow end thereof and in the closed position three cusps arcing inwardly between the legs, the outflow end of the leaflets touching with the three plateaus adjacent each other in the center of the outflow end of the valve.

27. The prosthesis of claim 26 wherein the cusps of the valve lay in face-to-face contact along a radial lines from the legs to the center, the width of the contact being from 0 to 2 mm in the center of the valve and from about 3 to about 7 mm about halfway between the center and the leg of the stent.

28. The prosthesis of claim 26 wherein the stent circumferentially is in the form of a right cylinder of constant diameter.

29. The prosthesis of claim 26 wherein the distance U from the inflow end of the stent to the bottom of the scallop on the outflow end of the stent is from about 0.50 to about 0.62 of the inside diameter of the stent.

30. The xenograft heart valve prosthesis of claim 26 wherein the depth of the scallops, as measured from the bottom of scallops on the outflow edge of the stent to the outflow end of the legs, is from 0.50 to about 0.65 of the internal diameter of the stent.

31. The prosthesis of claim 30 wherein the stent is circumferentially a right cylinder of constant diameter measured at both the inflow and outflow ends thereof.

32. In a xenograft heart valve prosthesis which comprises a circumferentially annular stent having an inflow end and an outflow end, the stent including an annular base and legs extending in the outflow direction therefrom, outflow end scallops, an annular sewing ring attached to and surrounding the stent, and a tissue valving member attached to the stent to form valve cusps, the cusps being located, respectively, in the scallops between the respective legs of the stent, the improvement wherein tissue cusps are formed of tissue fixed in the unstressed state and wherein the depth of the scallops, as measured from the bottom of scallops on the outflow edge of the stent to the outflow end of the legs, is from 0.50 to about 0.65 of the internal diameter of the stent, and wherein the tissue valving member is generally cylindrical in form and is formed to have three truncated triangular portions extending from the outflow end thereof intermediate between the legs forming three plateaus which lie adjacent each other when the valve is closed.

33. In a xenograft heart valve prosthesis which comprises a circumferentially annular stent having an inflow end and an outflow end, the stent including an annular base and legs extending in the outflow direction therefrom, outflow end scallops, an annular sewing ring attached to and surrounding the stent, and a tissue valving member attached to the stent to form valve cusps, the cusps being located, respectively, in the scallops between the respective legs of the stent, the improvement wherein tissue cusps are formed of tissue fixed in the unstressed state and wherein the valving member comprises a generally cylindrical tissue valve element having an inflow end and an outflow end, the outflow end of the valve element comprising three substantially equal portions, each of said portions having a truncated triangular edge forming a central plateau edge which extends centrally of such portion toward the outflow end of the valve, being positioned intermediate the legs of the stent, the valve element forming in the open position a cylinder with three plateaus on the outflow end thereof and in the closed position three cusps arcing inwardly between the legs, the outflow ends of the leaflets touching each other, the three plateaus adjacent each other in the center of the outflow end of the valve.

34. The prosthesis of claim 33 wherein the cusps of the valve lay in face-to-face contact along a radial line from the legs to the center, the width of the contact being from 0 to 2 mm in the center of the valve and from about 3 to about 7 mm about halfway between the center and the leg of the stent.

* * * * *